US006228070B1

(12) United States Patent
Mezzoli

(10) Patent No.: US 6,228,070 B1
(45) Date of Patent: May 8, 2001

(54) DEVICE FOR IRRIGATING OR WASHING THE NASAL CAVITIES AND THE RHINOPHARYNX

(75) Inventor: Giorgio Mezzoli, Lugo (IT)

(73) Assignee: Medical International Licensing, N.V., Curacao (AN)

(*) Notice: Subject to any disclaimer, the term of this patent is extended or adjusted under 35 U.S.C. 154(b) by 0 days.

(21) Appl. No.: 09/323,974

(22) Filed: Jun. 2, 1999

Related U.S. Application Data

(63) Continuation-in-part of application No. 08/913,519, filed on Sep. 19, 1997, now abandoned.

(30) Foreign Application Priority Data

Mar. 23, 1995 (IT) .......................................... B095A0126

(51) Int. Cl.[7] ...................................... A61M 5/00

(52) U.S. Cl. ...................................... 604/257; 604/94.01

(58) Field of Search .............................. 604/93.01, 94.01, 604/95.03, 257, 261, 262, 523, 403, 408, 35, 39, 41, 48, 911, 902

(56) References Cited

U.S. PATENT DOCUMENTS 1,604,518 * 10/1926 Kallmeyer .
1,755,754 * 4/1930 Wappler et al. .
3,847,145 * 11/1974 Grossan .
4,029,095 * 6/1977 Pena .
4,660,555 * 4/1987 Payton .
5,899,878 * 5/1999 Glassman ............................... 604/48

FOREIGN PATENT DOCUMENTS

0319501A2 * 6/1989 (EP) .

* cited by examiner

*Primary Examiner*—Anh-Tuan T. Nguyen
*Assistant Examiner*—LoAn H. Thanh
(74) *Attorney, Agent, or Firm*—Hedman & Costigan, P.C.

(57) ABSTRACT

A device for irrigating or washing the nasal cavities and the rhinopharynx which comprises a bell-shapes nozzle, adapted to be sealingly pressed to a nostril of a user, and a connection tube which connects the nozzle to a bag adapted to contain a solution; the bell-shaped nozzle has elliptical shaped sections orthogonal to the longitudinal axis of the nozzle, and has three holes radially arranged at the tip end of the nozzle for the outflow of a solution toward the three meatus of the nasal cavities, each hole communicating with a tubular joint positioned inside the nozzle and connected to the connection tube.

8 Claims, 3 Drawing Sheets

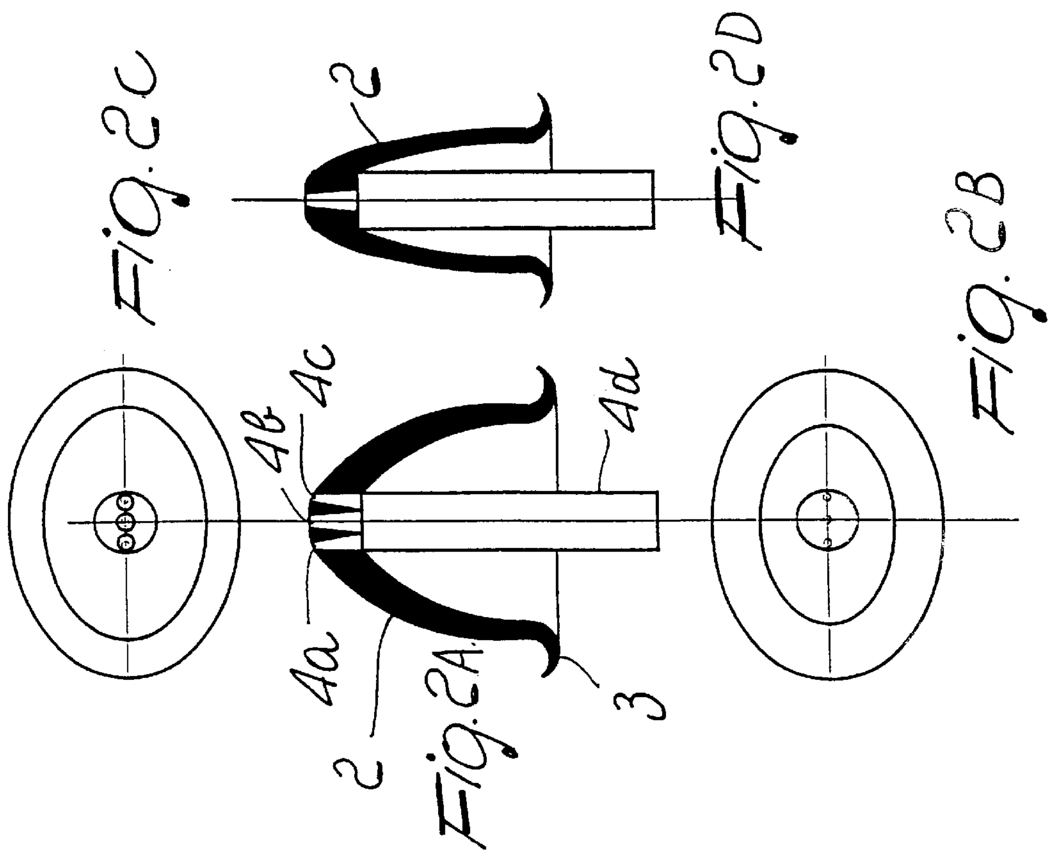
Fig. 2A
Fig. 2B
Fig. 2C
Fig. 2D
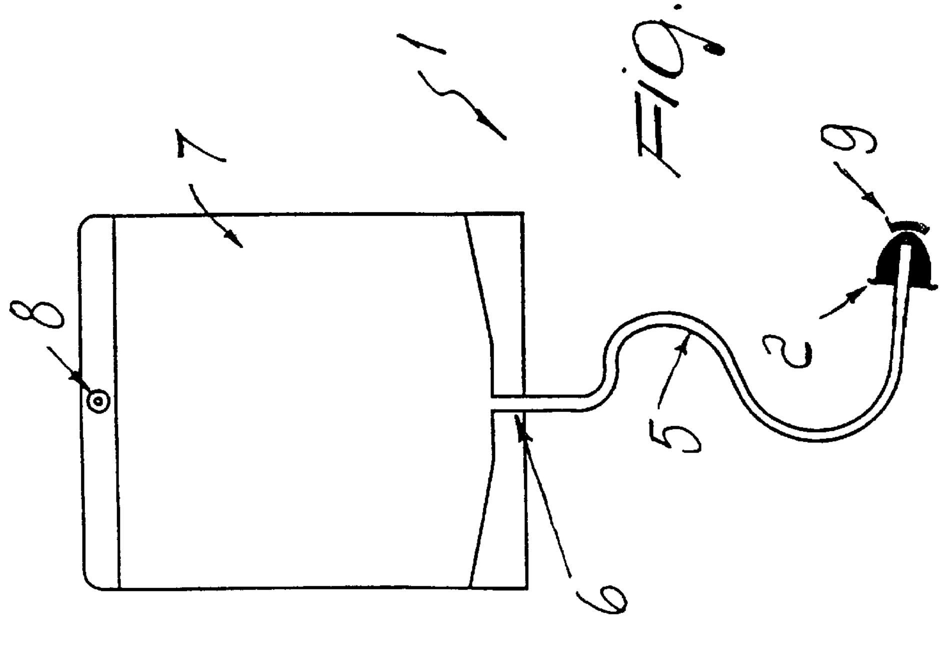
Fig. 1

DEVICE FOR IRRIGATING OR WASHING THE NASAL CAVITIES AND THE RHINOPHARYNX

CROSS-REFERENCE TO RELATED APPLICATION

The present application is a continuation-in-part of patent application Ser. No. 08/913,519, filed Sep. 19, 1997 now abandoned.

BACKGROUND OF THE INVENTION

The present invention relates to a device for irrigating or washing the meatus of the nasal cavities and the rhinopharynx.

The nasal cavities have the function of humidifying, purifying and warming the inhaled air and of dehumidifying and cooling the exhaled air. This system can suffer damages and thus become inefficacious as a consequence of the development of a pathology that can cause nasal respiratory difficulty because of inflammation of the nasal mucosa, stagnation of mucous or mucopurulent secretions, dust, allergens. In these circumstances the removal of the secretions which can be present inside the nasal cavities and also a stimulation of the nasal mucosa by means of a nasal washing, are necessary.

The substances that can be currently introduced into the nasal cavities can be either in form of drops or in nebulized form; in the first case it is necessary to introduce the solution with the head leaned backwards while the removal of the washing product occurs by forced expiration through the nasal cavities, or by deglutition (the head of the subject has to be leaned backwards in order to avoid that during the introduction the solution comes out by infiltrating between the nasal vestibule and the opening of the container of the solution); whereas in the second case the nebulization occurs with spray bottles that often use propellents that can be irritating for the nasal mucosa.

In the typologies of the mentioned interventions, the amount of substance that can be introduced into the nasal cavities is always very small.

The only equipments that allow to carry out an efficacious washing of the nasal cavities and of the rhinopharynx with great amounts of solution are of thermal or ambulatory type and therefore rather expensive; such equipments require, for their use, qualified personnel and involve from time to time the sterilization of some components. Other components, not intended to be cleaned after each use, yet are subject to be in contact and to become dirty with the substances removed from the washing operations. The user, or the authorized personnel, is then subjected, during the washing operation, to dirty the fingers that grip the delivery nozzle of the solution.

EP 0 319 501 (Loefstedt) discloses a device for administering a solution into a nasal cavity comprising a compressible container containing the solution to be administered and an olive shaped conical nozzle to be placed into the nose. The solution is pumped via the nozzle into the nose by squeezing the container.

The nozzle is a truncated half olive, which must be conical and has a circular base; the diameter of the base is 15–23 mm, preferably 19 mm. The upper part of the nozzle, which is in contact with the nostril, is also conical and has a circular opening with a diameter preferably between 3–10 mm.

Said upper part of the olive is inserted into the nose and the nasal cavity can be completely filled with the solution by pumping it by compressing the container, then the solution from the nasal cavity returns into the container by releasing the container.

The device disclosed by EP 0 319 501 shows several serious drawbacks. The upper part of the nozzle has a truncated conical shape which does not fit the shape of the nostril (the nostrils have substantially oval or elliptical openings) and therefore must be pushed inside the nose (see FIGS. 3 and 4) by the user with the risk of redness of the nostril, uncomfortable position, pain and damage of the nasal mucosa with risk of damages of the nasal septum and of the inferior turbinates. Then, when the solution from the nasal cavity returns into the container, it contains mucous or substances secreted by the nasal cavity and, as consequence, it plugs the opening of the nozzle preventing the solution to return into the container.

The nozzle described has a central opening and it is inserted into the nose without a specific orientation. Desiring to direct the solution stream toward specific portions of the nasal cavity, the operator (especially if without specific training or knowledge) tends to move the upper part of the nozzle inside the nasal cavity with serious risks of damages of the nasal mucosa with possibility of epistaxis, and other damages as above said.

Then, the solution is administered into the nasal cavity by pumping it from the compressible container. In case of a strong compression (pressure) of the container, it could determine a strong stream of the solution into the nasal cavity with risk of serious internal damages and rupture of the wall of vessels.

U.S. Pat. No. 4,660,555 (Payton) discloses an oxygen delivery and administration system comprising a nosepiece having a conical section (with a circular base) and a truncated tip, completely inserted within the nose, having a primary axial oxygen passageway and lateral secondary oxygen passageways. Said lateral secondary passageways, directed not toward the meatus but toward the internal lateral walls of the nasal cavity, is provided in case the primary passageway becomes plugged with mucous.

The nozzle of U.S. Pat. No. 4,660,555 is disclosed only for the administration of oxygen; in fact its structure could not suggest the use of said nozzle for the administration of a solution into the nasal cavity. Further, the nozzle requiring to be inserted completely into the nose, and comprises an anular skirt which extends rearwardly pushing on the vestibule preventing the nozzle coming out from the nose. These technical features of the nozzle necessarily cause serious damages to the mucosa, redness, bleeding and risk of perforation of the nasal septum.

In practice no equipment for domestic use exists on the market that allow to sprinkle remarkable amounts of liquids into the nasal cavities and the rhinopharynx in an easy, simple, inexpensive and hygienic manner and without any risk due to a wrong use.

SUMMARY OF THE INVENTION

The aim of the present invention is to obviate the drawbacks of conventional devices, by providing a device for a correct positioning to the nostril, and for specifically irrigating or washing the three meatus of the nasal cavities and the rhinopharynx that allows to carry out such operations in a simple and hygienic way.

Within the scope of this aim, another object of the present invention is to provide a device which is structurally simple, easy to be manufactured, safe in use, efficacious in operation, and also having a relatively low cost.

This aim and these objects are achieved by the present device for correctly and specifically irrigating or washing the meatus of the nasal cavities and the rhinopharynx which comprises a bell-shaped nozzle which is adapted to be sealingly pressed to one of nostrils of the user, who places his head slightly leaned forwards or sideways, said nozzle having elliptical shaped sections orthogonal to the longitudinal axis of the nozzle, said sections having a major symmetry axis (a) and a minor axis (b) of different length (as clearly shown in FIGS. 2 and 3). The nozzle according to the invention comprises a tip end, which is sealingly pressed to the nostril, and three holes arranged at the tip end of the nozzle for the outflow of a solution toward the nasal cavities, these three holes being radially arranged on the symmetry plane which includes the major symmetry axes (a) of said nozzle.

Each of the three holes communicates with a tubular joint, positioned inside the nozzle and connected to a tube which connects the nozzle to a bag or the like adapted to contain the washing solution. The bag or the like supplies, advantageously by gravity, the solution to be sprinkled, the solution and the washing product flowing along the meatus of a nasal cavity and through the rhinopharynx into the contralateral nasal cavity and flowing outside through the vestibule of the contralateral nasal cavity.

The devices described in the state of the art are conical nozzles with a circular base and therefore these devices when placed into the nostril do not have a specific orientation and, as consequence, the holes of the truncated nozzles as well as the streams of the washing solutions are casually directed inside the nasal cavity and the washing process is realized in a casual way.

On the contrary, the device according to the present invention is a bell-shaped nozzle having elliptical shaped sections orthogonal to the longitudinal axis of the nozzle and the three holes are arranged at the tip end of the nozzle and radially arranged on the symmetry plane which includes the major symmetry axes (a) of the nozzle. Therefore, once the nozzle is positioned, it fits to the nostril (which has a substantially elliptical opening) and, as consequence, there is only one possible positioning of the nozzle into the nostril. Once the positioning is performed, each of the three holes is univocally oriented and each of the three streams (A, B, C of FIG. 6) is directed toward each of the three meatus (A1, B1, C1), and the washing process of the meatus is improved and optimized.

According to a further aspect, the nozzle according to the invention comprises a flared edge portion, opposite to the tip end provided with the three holes, adapted to prevent the possible outflow of the solution along the tube of conducting and to avoid the user dirties his finger with the solution and the substances removed by the washing.

According to another further aspect, the nozzle according to the invention is internally hollow so as to be squeezable; that allows a better and easier handling of the nozzle by the user.

BRIEF DESCRIPTION OF THE DRAWINGS

Further characteristics of the present invention will become apparent from the detailed description of a preferred, but not exclusive, embodiment of a device for correctly and efficiently irrigating or washing the meatus of the nasal cavities and the rhinopharynx according to the invention, illustrated only by way of non-limitative example in the accompanying drawings, wherein:

FIG. 1 is a front schematic view of a device for irrigating or washing the nasal cavities and the rhinopharynx according to the invention; the device can be formed by separable nozzle, connecting tube and bag or they can form a single monolithic body, the bag containing already the solution to be sprinkled;

FIG. 2*a* is a cross-sectional front elevation view of a nozzle of the device of FIG. 1, according to a first embodiment thereof wherein the nozzle is internally hollow and squeezable;

FIG. 2*b* is a bottom plan view of the nozzle of FIG. 2*a;*

FIG. 2*c* is a top plan view of the nozzle of FIG. 2*a;*

FIG. 2*d.* is a cross-sectional end elevational view of the nozzle of FIG. 2*a;*

DESCRIPTION OF THE PREFERRED EMBODIMENTS

Figure 3C:
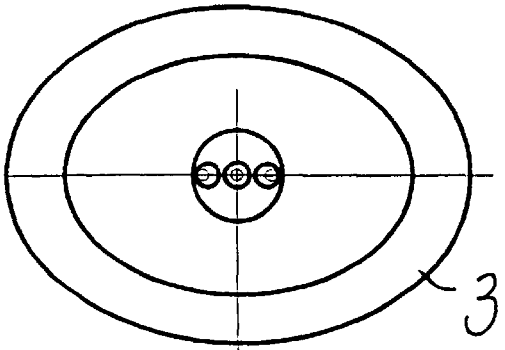
FIG. 3*c* is a top plan view of the nozzle of FIG. 3*a;*
Figure 3A:
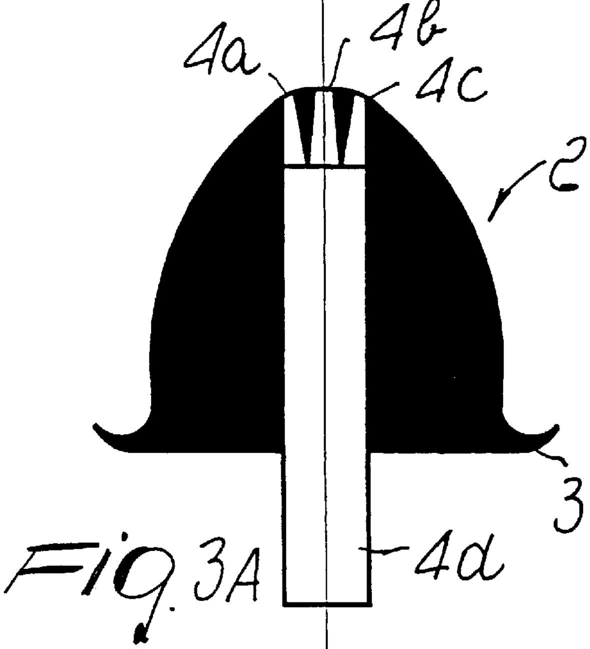
FIG. 3*a* is a cross-sectional front elevation view of a nozzle of the device of FIG. 1, according to another embodiment thereof.
Figure 3D:
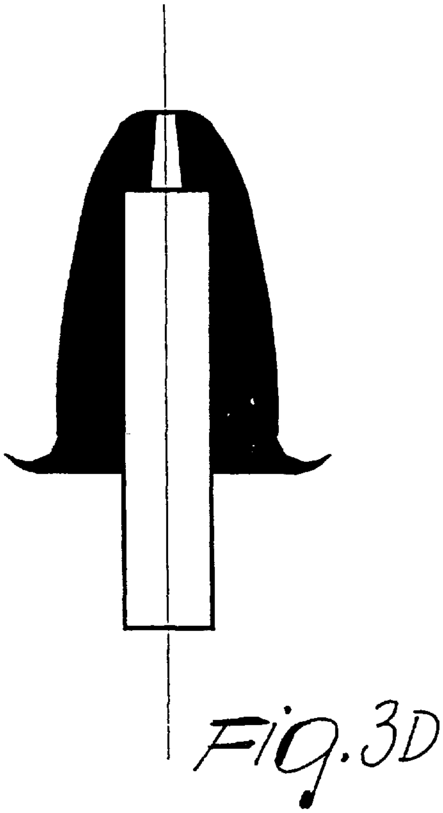
FIG. 3*d* is a cross-sectional end elevational view of the nozzle of FIG. 3*a;*
Figure 3B:
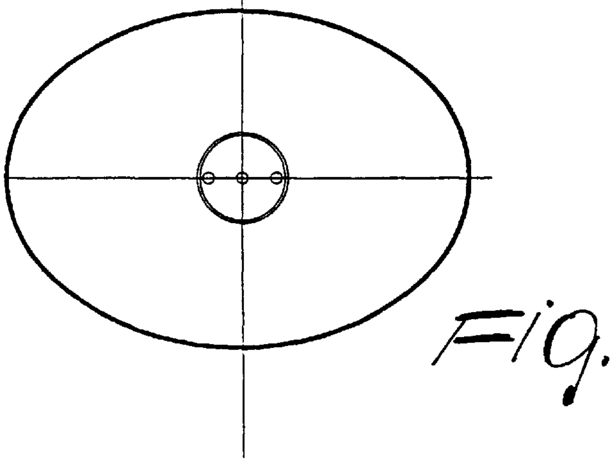
FIG. 3*b* is a bottom plan view of the nozzle of FIG. 3*a;*

With reference to the above figures, the device for irrigating or washing the meatus of the nasal cavities and the rhinopharynx according to the invention is generally designated by the reference numeral 1.

The device 1 comprises a bell-shaped nozzle 2 that is adapted to be sealingly pressed to the nostril of the nose of the user. The particular shape of the nozzle allows to fit to nostrils of various typologies, by taking advantage of the fact that a nostril has a substantial oval or elliptical opening; it is expected to manufacture the bell in many sizes if necessary.

The bell-shaped nozzle 2 has a shape such that it is adapted to be sealingly pressed to one of the nostrils of the user, who places his head slightly leaned forwards or sideways. The nozzle 2 has elliptical shaped sections orthogonal to the longitudinal axis of the nozzle, said sections having a major symmetry axis (a) and a minor axis (b) of different length (as clearly shown in FIGS. 2 and 3). Therefore axis (a) and axis (b) cannot have the same length. Nozzle 2 comprises a tip end, which is sealingly pressed to the nostril, and three holes 4*a*, 4*b*, 4*c* arranged at the tip end of the nozzle for the outflow of a solution toward the nasal cavities, these three holes are radially arranged on the symmetry plane which includes the major symmetry axes (a) of said nozzle.

The bell-shaped nozzle 2 is manufactured by moulding materials like plastics or rubber and in the embodiment of FIGS. 2*a*–2*d* it is hollow in the portion 4*e* so as to render the nozzle squeezable and the section of the walls can vary in order to provide the required softness and stiffness; the nozzle 2 has a solid section 4*f* in the other prospected embodiment of FIGS. 3*a*–3*d*.

The nozzle 2, in the different embodiments, has edge 3 slightly cone-shaped and leaned towards the outside and is slightly squeezed so as to have a substantially elliptical section according to the planes orthogonal to the longitudinal axis of the nozzle; the flared edge portion 3 is adapted to prevent the possible outflow of the solution along the tube of conduction 5 and to avoid that the user dirties his fingers with the solution and the substances removed by the washing.

Figure 6:
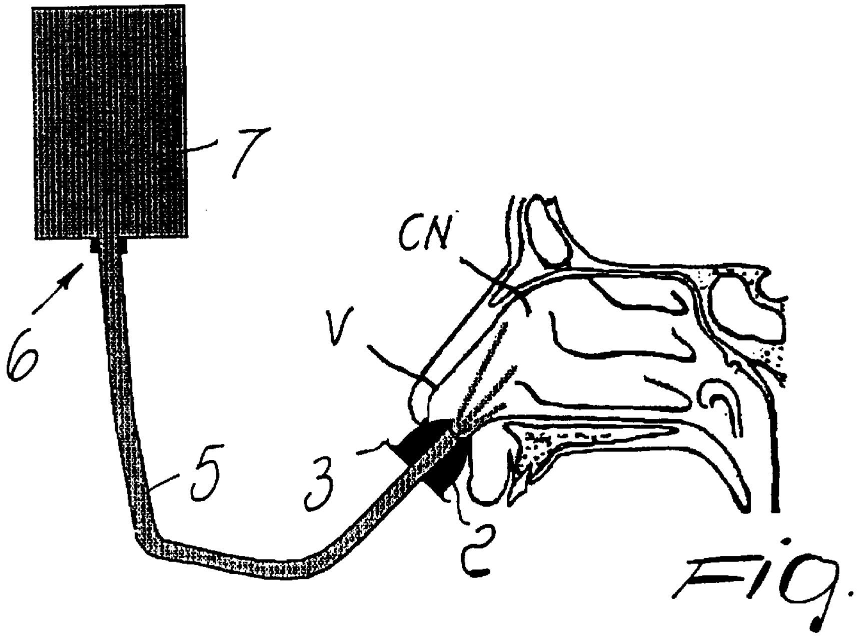
FIG. 6 is a view of a coupling of the device to the vestibule of a nasal cavity and the univocal orientation of each of the three holes toward each of the three meatus.

The nozzle 2 has at three holes 4*a*, 4*b*, 4*c*, for the outflow of the liquid, having slightly diverging streams A, B, C from each other (as shown in FIG. 6), each of these streams specifically directed toward each of the three meatus A1, B1, C1 (FIG. 6). The three holes are arranged at the tip end of the nozzle and are radially arranged on the symmetry plane which includes the major symmetry axes (a) of the nozzle, in such a way that thanks to the specific elliptical shape of the bell-shaped nozzle of the invention, ones the nozzle is set into the nostril in the only orientation possible, the three holes are univocally oriented towards the three meatus of the nasal cavities and the three streams of the washing solution are sprinkled in the nasal cavities and rhinopharynx in the best manner.

It is clear from the description and from the Figures that a nozzle having a conical nozzle, therefore having circular sections orthogonal to the longitudinal axis of the nozzle, are not included in the nozzle of the invention, because these conical nozzles are inserted into the nostril without a specific orientation and, as consequence, the holes and the streams are not directed toward each of the meatus but in a casual way. As consequence, the washing process performed with a conical nozzle suffers with the serious drawbacks indicated in the state of the art and represents the techinical problem which is solved by the elliptical nozzle of the present invention.

The holes 4*a*, 4*b*, 4*c* of the nozzle communicate with a tubular joint 4*d* to couple with an end of a conduction 5, said tube, at the other end, has means 6 for connection to a bag 7 or the like for supplying, advantageously by gravity, the solution to be sprinkled. In the particular case illustrated in FIG. 1 the connection means consist of a direct clamp of the tube to the bag, but optionally the connection can occur by means of perforating point, screw or bayonet coupling or the like. Preferably, the three holes 4*a*, 4*b*, 4*c* communicate with the three corresponding slightly diverging small tubes, and these small tubes communicate with the tubular joint 4*d* (FIGS. 2A, 2D, 3A, 3D).

Conveniently, the bag 7 is flexible and provided with an eyelet 8, in order to be clamped, for, instance with a suction-cup, in a position lifted with respect to the head of the user.

The bag 7 can be filled with solutions of any kind which are simply detergent, slightly disinfectant or even therapeutic.

The device 1 is of a disposable type and is contained in a sterile packaging: conveniently, nozzle, tube and bag form a single or monolithic body and the bag contains already the solution to be sprinkled in a sterile confection; in this latter case the nozzle 2 can have a seal such as a tear-off sealing plug 9, that is removed immediately before the use; alternatively the nozzle is inserted into a removable protecting cap before the use.

Figure 4:
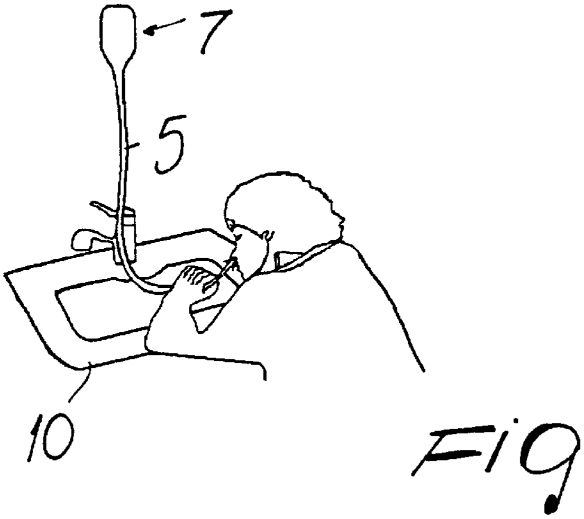
FIG. 4 is a perspective view of a device according to the invention in condition of use.

The operation of the device according to the invention is as follows: the user, possibly after having warmed the content of the bag 7 up to about 37° C. (for instance by immersion in hot water), fixes the bag 7 in lifted position and places his head slightly leaned forwards or sideways on a collecting basin 10 that can be a washbasin or the like (position illustrated in FIG. 4).

Figure 5:
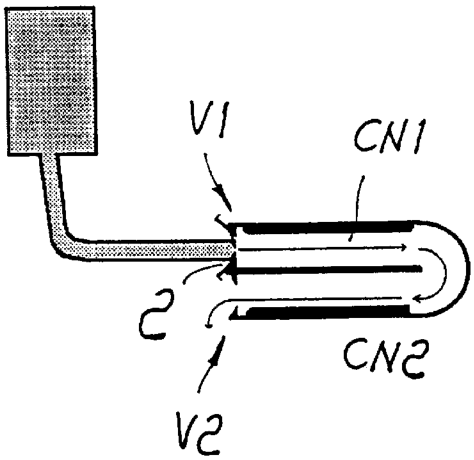
FIG. 5 is a schematic top view of the path of the washing solution into the nasal cavities.

Once the plug 9 is removed, after having strangled the tube in order to avoid undue outflow of the solution, the user sealingly presses the bell-shaped nozzle 2 to the nostril; thanks to the particular the elliptical shape, the nozzle 2 fits to the nostril (which has a substantially oval or elliptical opening) of the user and, as consequence, there is only one possible positioning of the nozzle into the nostril; once the positioning is performed, each of the three holes will be univocally oriented toward each of the three meatus; then by releasing the strangling of the tube, each of the three streams are directed into each of the three (high, middle and low) meatus; the solution and the product of the washing flow along the meatus of the nasal cavity CN1, go through the rhinopharynx to flow into the controlateral nasal cavity CN2 and flow outside through the vestibule V of the controlateral nasal cavity V2 (as shown in FIGS. 5 and 6).

The pressure of washing can be lowered and is adjustable, together with the flow of the solution, by simply raising or lowering the bag with respect to the height at which the user's nose is, therefore the possibility that detrimental overpressures may occur to the mucous membranes during the use does not exist.

In this way the device according to the invention has achieved the intended aims. The device according to the invention is susceptible to many modifications and variations all of which are included in the scope of the inventive concept. Moreover all the details are replaceable by other technically equivalent-details. In practice the materials used, as well as the shapes and sizes, can be any without abandoning the protection scope of the appended claims.

What I claim is:

1. A device for irrigating or washing the nasal cavities and the rhinopharynx which comprises a bell-shapes nozzle, adapted to be sealingly pressed to a nostril of a user, and a connection tube which connects said nozzle to a bag adapted to contain a solution, wherein said bell-shaped nozzle has elliptical shaped sections orthogonal to the longitudinal axis of the nozzle, said sections having a major symmetry axis and a minor symmetry axis of different length; and wherein said bell-shaped nozzle has a tip end and has three holes arranged at said tip end of said nozzle for the outflow of a solution in three streams diverging from each other toward each of the three meatus of the nasal cavities, each hole communicating with a tubular joint positioned inside said nozzle and connected to said connection tube, said holes being radially arranged on the symmetry plane which includes the major symmetry axes (a) of said nozzle.

2. A device according to claim 1, wherein said bell-shaped nozzle has a flared edge portion, opposite to the tip end provided with said three holes.

3. A device according to claim 1, wherein said bell-shaped nozzle in internally hollow so as to be squeezable.

4. A device according to claim 1, wherein said device is of the disposable type.

5. A device according to claim 1, wherein said nozzle, said tube and said bag are monolithic, said bag containing the solution to be sprinkled.

6. A device according to claim 1, wherein said nozzle is made of plastics for medical use and a solution contained therein is adapted to be warmed, before use, at temperature of about 37° C.

7. A device according to claim 1, wherein said tubular joint is connected at one end to said bell-shaped nozzle, in direct contact with said three holes and has an opposite end which is arranged inside said hollow bell-shaped nozzle and is spaced from internal walls of said nozzle.

8. A device for irrigating or washing the nasal cavities and the rhinopharynx, corresponding to FIG. 2 or 3 of the accompanying drawing, which comprises a bell-shaped nozzle, adapted to be sealingly pressed to a nostril of a user, and a connection tube which connects said nozzle to a bag adapted to contain a solution, wherein said bell-shaped nozzle has elliptical shaped sections orthogonal to the longitudinal axis of the nozzle, said sections having a major symmetry axis and a minor symmetry axis of different length; and wherein said bell-shaped nozzle has a tip end and has three holes arranged at said tip end of said nozzle for the outflow of a solution in three streams diverging from each other toward each of the three meatus of the nasal cavities, each hole communicating with a tubular joint positioned inside said nozzle and connected to said connection tube, said holes being radially arranged on the symmetry plane which includes the major symmetry axes (a) of said nozzle.

* * * * *